United States Patent [19]

Pandey et al.

[11] Patent Number: 5,093,349
[45] Date of Patent: Mar. 3, 1992

[54] PHOTOSENSITIZING AGENTS

[75] Inventors: Ravindra K. Pandey, Buffalo; Thomas J. Dougherty, Grand Island, both of N.Y.

[73] Assignee: Health Research Inc., Buffalo, N.Y.

[21] Appl. No.: 597,786

[22] Filed: Oct. 15, 1990

Related U.S. Application Data

[63] Continuation of Ser. No. 221,804, Jul. 20, 1988, Pat. No. 5,002,962.

[51] Int. Cl.$^5$ .................... A61K 31/40; C07D 487/22
[52] U.S. Cl. .................................. 514/410; 540/145
[58] Field of Search ........................ 514/410; 540/145

[56] References Cited

U.S. PATENT DOCUMENTS 4,849,207 7/1989 Sakata et al. .................... 424/1.1
4,877,872 10/1989 Morgan et al. .................... 540/145

FOREIGN PATENT DOCUMENTS 63-101384 5/1988 Japan .

Primary Examiner—Richard L. Raymond
Attorney, Agent, or Firm—Morrison & Foerster

[57] ABSTRACT

New classes of photosensitizing compounds useful in photodynamic therapy are disclosed. These compounds are simplified dimers and polymers of monohydroxy deuteroporphyrins, hydrophobic ethers of these monomers, and red light-absorbing derivatives of methyl pheophorbide-a.

6 Claims, 2 Drawing Sheets

PORPHYRIN
DERIVATIVE-2

PORPHYRIN
DERIVATIVE-4

PHOTOSENSITIZING AGENTS

This application is a continuation, of application Ser. No. 07/221,804 filed, July 20, 1988, now U.S. Pat. No. 5,002,962.

TECHNICAL FIELD

The invention relates to the use of porphyrin related compounds in photodynamic therapy (PDT). In particular, it relates to the use of certain simplified hematoporphyrin derivatives and of compounds which absorb light in the 660 nm range.

BACKGROUND ART

It has been known for some time that porphyrin related compounds accumulate at higher concentrations in tumor tissue as compared to normal tissue, and that irradiation of these compounds using light of the proper wavelength results in an energized form which, upon decay, results in cytotoxicity. It is believed that excitation of the porphyrin or related material results in the formation of singlet oxygen which is in fact the toxic agent. However, the compounds administered apparently do not degrade in this process.

An extensive literature relating to the use of "hematoporphyrin derivative" (HPD) describes this process utilizing a preparation obtained when hematoporphyrin dichloride is treated using the procedure of Lipson, R. L., et al, *J. National Cancer Inst* (1961) 26:1-8. More recently, it has been shown that if this hematoporphyrin derivative is treated at a suitable pH, aggregation occurs and the active material in the mixture can be prepared in crude form as a size segregated aggregate (see, for example, U.S. Pat. No. 4,649,151, incorporated herein by reference). This preparation is commercially available under the trademark Photofrin II.

It is clear that the preparation marketed as the Photofrin II composition is itself a mixture. It is known that the mixture contains porphyrins joined by ether linkages (Dougherty, T. J., et al, *Adv Exp Med Biol* (1983) 160:3-13), and more recently, Kessel, D., et al, *Photochem Photobiol* (1987) 46:463-568, has shown that ester linked porphyrins are contained in this mixture as well. Scourides, P. A., et al, *Cancer Res* (1987) 47:3439-3445 have synthesized an oligomeric mixture of ether linked porphyrins starting from hematoporphyrin dimethyl esters. The mixture was active in PDT, but was as complex a mixture as the Photofrin II preparation. Dimers of hematoporphyrin joined by ester linkages have also been prepared by Pandey, R. K., et al, *Cancer Res* (in press) and the dimers prepared were shown to be absent from the mixture in the Photofrin II composition as well as inactive in an in vitro assay.

Thus, it is known in the art that some elements of a mixture prepared when HPD is aggregated and segregated into higher molecular weight components are active in photodynamic therapy. However, it is not settled and not known what all of these active ingredients are, nor has it been possible to prepare single compound compositions which are useful in PDT. It would clearly be advantageous to utilize a purified and defined composition in this therapeutic method rather than a complex mixture, which while effective, is not completely understood.

DISCLOSURE OF THE INVENTION

The invention is directed to compounds newly found to be useful in photodynamic therapy in a manner similar to that known for Photofrin II compositions. These compounds include 1) simple dimers or "porphyrin derivatives" of monosubstituted deuteroporphyrins, 2) hydrophobic ethers of hematoporphyrin or its esters and 3) hydrophobic ethers of pheophorbol or chlorin derivatives.

Thus, in one aspect, the invention is directed to compounds which are dimers or polymer mixtures of either 2-(1-hydroxyethyl)deuteroporphyrin or the corresponding 4-(1-hydroxyethyl)deuteroporphyrin or their alkyl esters. In a second aspect, the invention is directed to compounds which are diethers of a 6-25 C hydrocarbyl group with hematoporphyrin or its esters. In a third aspect, the invention is directed to tetrapyrole compounds which absorb red light as opposed to shorter wavelengths. These compounds are derivatives of methyl pheophorbide-a which can be isolated from natural sources and converted to higher molecular weight ethers in the A-ring, as well as the hydrolyzed forms thereof.

In other aspects, the invention is directed to pharmaceutical compositions containing the compounds of the invention as active ingredients and to methods of conducting photodynamic therapy using the compounds and compositions of the invention.

In still another aspect, the invention is directed to the compounds of the invention conjugated to a ligand which is capable of binding a specific receptor such as a cellular receptor, or an antibody which is capable of binding to a particular antigen and to compositions containing these conjugates and methods of conducting photodynamic therapy using the conjugates and their compositions.

MODES OF CARRYING OUT THE INVENTION

The invention provides three major classes of compounds which are useful in photodynamic therapy.

Derivatives of (1-Hydroxyethyl)deuteroporphyrin

The first class of compounds are the simple dimers of the esters of 2(1-hydroxyethyl)deuteroporphyrin and the isomeric 4(1-hydroxyethyl)deuteroporphyrin ester, and the "porphyrin derivatives" (PD) obtained by treatment of the carboxylic acid forms of these compounds. These compositions are derived from compounds of the formula

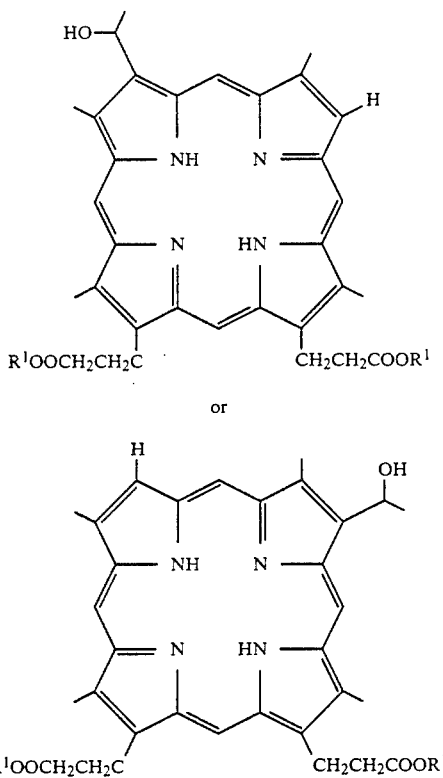

wherein $R^1$ is H or alkyl (1–6C), by treatment of the free acid under acetylating and dehydrating conditions to form the porphyrin derivative, or of the dialkyl ester under controlled conditions to form the dimer. The porphyrin derivative, PD-2 or PD-4, is obtained by treating the compound of formula 1 or 2 respectively in acetic acid/$H_2SO_4$ followed by hydrolysis in aqueous base. The dimer is conveniently prepared by treating the alkyl diester, of the 2-carboxyethyl substituents, preferably the dimethyl ester, first in HBr/acetic acid, followed by addition of from hemin dimethyl ester using the method of Smith et al, *Ad Exp Med Biol* (1985) 193:277–292. Treatment of the appropriate copper complex with acetic anhydride/stannic chloride gave a mixture of the mono- and diacetyl derivatives by the Friedel Crafts reaction; the monoacetyl derivatives were separated from the diacetyl derivative by column chromatography. The 2- and 4-monoacetyl isomers were separated by a preparative HPLC as described by Smith (supra) and the references cited therein. Copper was removed from the complex using the method of Smith and Pandey, J., *Heterocyclic Chem* (1983) 20:1383–1388, using trifluoroacetic acid/sulfuric acid, and the acetyl groups were reduced to the corresponding alcohols using sodium borohydride. The resulting compounds were then optionally hydrolyzed or retained as the methyl esters.

The hydrolyzed compounds were converted to the analogous "porphyrin derivatives" using acetic acid/sulfuric acid followed by treatment with 0.1N NaOH as shown in Reaction Scheme 1.

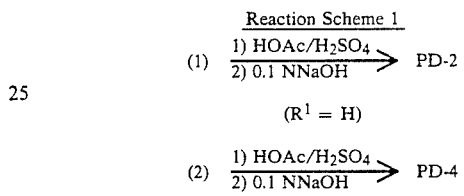

Figure 1A:
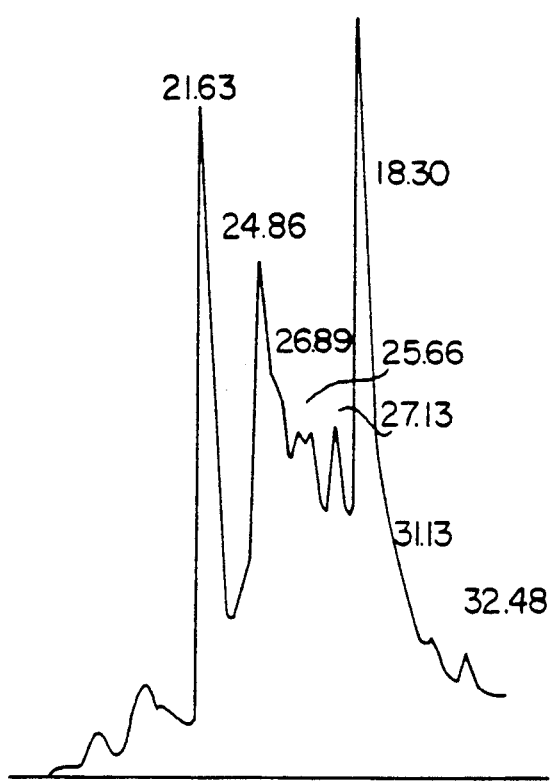
FIG. 1a and 1b show the HPLC trace obtained on conversion of the monosubstituted deuteroporphyrins to the corresponding porphyrin derivatives (PD).
Figure 1B:
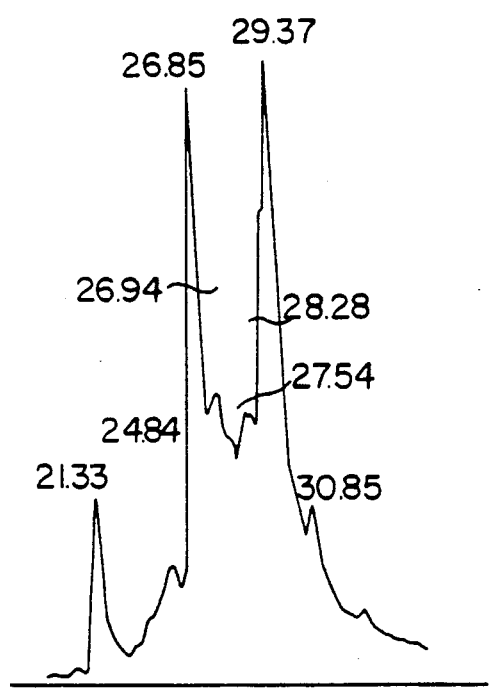

The resulting mixtures gave the HPLC patterns shown in FIG. 1. These patterns are substantially less complex than those exhibited by the Photofrin II compositions known in the art, but it is clear that mixtures of products result. Peaks with retention times of 2.63 minutes in porphyrin derivative-2 and 21.33 in porphyrin derivative-4 are due to the presence of the dehydration products of the starting materials.

Figure 2:
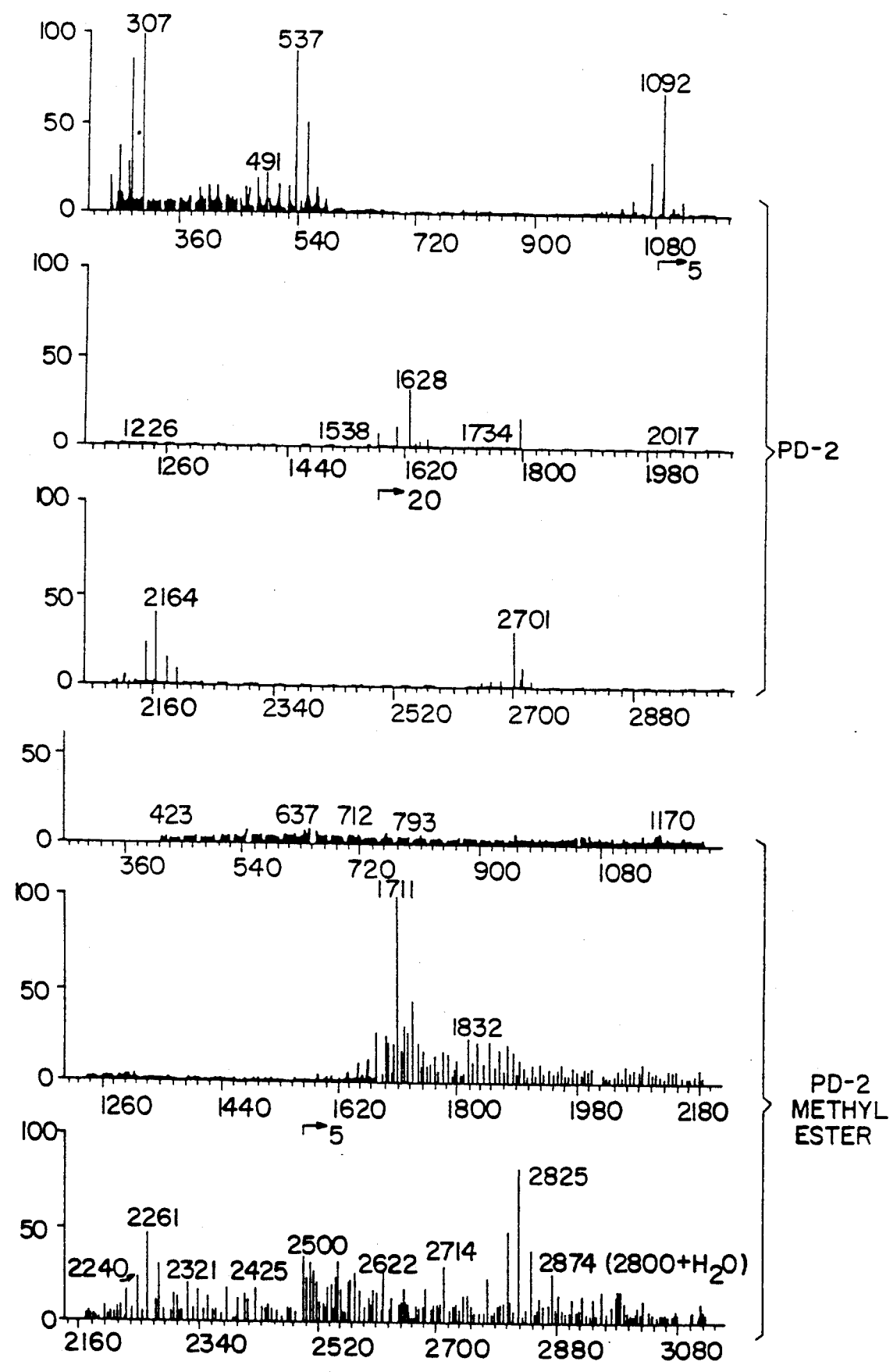
FIG. 2a and 2b show the FAB mass spectrum for PD-2 and PD-2 methyl ester.

The FAB mass spectra of these products (PD-2 and PD-4) were also obtained and were repeated after esterification to the methyl ester. The results for PD-2 and its methyl ester derivative are shown in FIG. 2. These patterns show that the PD-2 mixture contains unconjugated deuteroporphyrin and conjugates containing 2–5

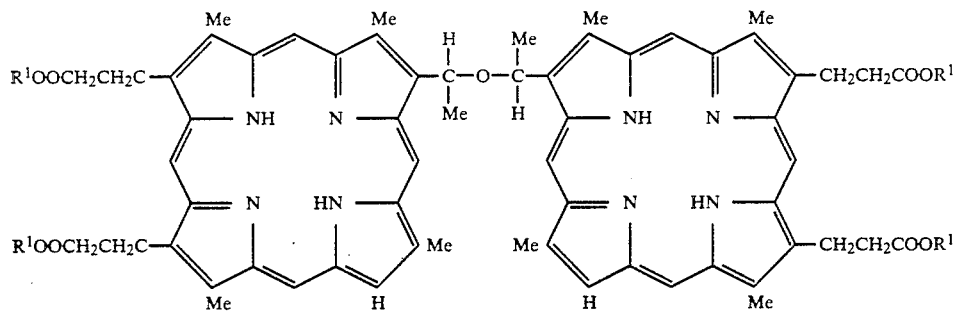

an equimolar amount of the starting material of formula (1) or (2). One resulting dimer or its hydrolyzed form is of the formula designated herein "dimer-2" wherein $R^1$ is H or alkyl (1–6C); the corresponding dimer-4 is prepared using 4-(1-hydroxyethyl)deuteroporphyrin dimethyl ester as starting material.

In more detail, and in an illustrative procedure, the simplified dimers and polymers of PD-2 and PD-4 prepared from the singly substituted (by 1-hydroxyethyl) deuteroporphyrins were synthesized using procedures analogous to those used for preparation of hematoporphyrin derivative. The starting materials were prepared porphyrins linked as oligomers. The M/E peak at 2800 in the FAB mass spectrum of the methyl ester indicates that in the pentamer, 2 of the 5 porphyrins are linked by an ether linkage, and the remainder by 3 ester linkages. Other peaks correspond to a dimer with an ether linkage; a trimer with 1 ether and 1 ester linkage; and a tetramer with 1 ether and 2 ester linkages.

The ether dimers of the 2(1-hydroxyethyl) deuteroporphyrin and the corresponding 4-substituted deuteroporphyrin were obtained by utilizing the methyl ester derivatives of the starting material rather than the free acid form as shown in Reaction Scheme 2.

Reaction Scheme 2

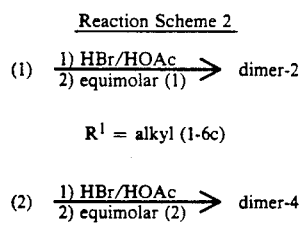

Of course the isomeric forms of the dimers could also be obtained by adding compound of formula (1) in the second step to the reaction mixture containing the compound of formula (2) and vice versa.

In this synthesis, 25 mg of starting material was reacted with 32% HBr/acetic acid (2 ml) with stirring in a sealed flask at room temperature. The solvent was removed under high vacuum and the bromo derivative obtained was redissolved in dry dichloromethane. An additional 25 mg of the starting porphyrin material (2(1-hydroxyethyl)deuteroporphyrin dimethyl ester) was added. The reaction mixture was stirred at room temperature for 5 minutes under nitrogen and 50 ml dichloromethane was added. The mixture was washed with water and the dichloromethane layer separated and dried over anhydrous sodium sulfate. Evaporation of solvent and purification of the residue afforded the desired dimer product, shown in Scheme 2 in 58% yield. The structure was confirmed by mass spectroscopy and by NMR. (Pandey and Dougherty, *Photochem Photobiol* (1988) 47:769-777.)

The dimer of the corresponding 4-(1-hydroxyethyl)-deuteroporphyrin dimethyl ester was obtained in 52% yield and confirmed by mass spectroscopy and NMR.

The biological activity of PD-2, PD-4, and the corresponding dimer-2 and dimer-4 were tested for photosensitizing activity using an in vivo mouse tumor assay. The results are shown in Table 1.

TABLE 1

| Material | Dose, mg/kg | Tumor Response | |
| --- | --- | --- | --- |
| | | Day 1-2 | Day 7 |
| Photofrin II | 4.2 | 10/10 | 5/10 |
| | 5.0 | 10/10 | 7/10 |
| | 6.5 | 10/10 | 9/10 |
| Dimer-2 | 5.0 | 10/10 | 3/10 |
| | 6.5 | 10/10 | 7/10 |
| Dimer-4 | 5.0 | 9/9 | 2/8 |
| PD-2 | 4.2 | 6/6 | 3/6 |
| PD-4 | 4.2 | 6/6 | 4/6 |

As shown in Table 1, the compounds of the invention have similar activities to the Photofrin II compositions.

Hydrophobic Hp Ethers

The second major group of compounds of the invention comprises compounds of the formula

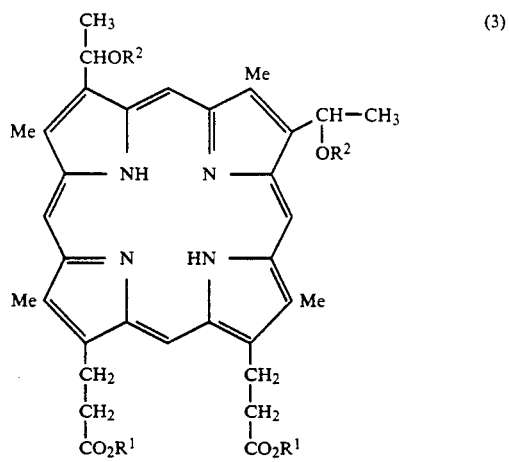

wherein $R^2$ is a saturated or unsaturated hydrocarbyl residue of 6-25 carbons. These hydrophobic diethers of hematoporphyrin are themselves useful in photodynamic therapy as will be further shown below. The saturated/unsaturated hydrocarbyl group may be a straight or branched chain hydrocarbon containing 1-3 pi bonds. Exemplary of such hydrocarbyl groups are hexyl, decyl, dodecyl, 3-methyl dodecyl, 4-methyl tetradecyl, and phytyl. By way of illustration, the synthesis of the phytyl ethers is described below:

The phytyl ether derivative of hematoporphyrin dimethyl ester was prepared by reacting 50 mg hematoporphyrin dimethyl ester with 32% HBr/acetic acid as described above for preparing the dimers. The bromo derivative was redissolved in dried dichloromethane and 2 ml phytyl alcohol was added. The reaction was stirred for 30 minutes at room temperature under nitrogen and the product purified as described above. The porphyrin derivative was obtained as a sticky solid and the structure confirmed by NMR and mass spectroscopy. The resulting phytyl ether of formula (3) wherein both $R^1$ are $CH_3$ and both $R^2$ are phytyl, showed similar anti-tumor activity to Photofrin II compositions at a dose of 5 mg/kg; phytyl esters prepared from the propionic acid side chains ($R^1$ is phytyl) did not show activity.

Thus, the invention is also directed to the use of compounds of the formula (3) wherein $R^1$ is H or alkyl (1-6C) and $R^2$ is a hydrophobic group which is a straight or branched chain saturated or unsaturated hydrocarbyl of 6-25 carbons.

Red Light-Absorbing Compounds

Also useful as photosensitizing agents in tumor treatment are a group of red light-absorbing monomers which are prepared from methyl pheophorbide-a. These compounds absorb at 665 nm, approximately, and show tumorcidal activity in the standard bioassays described above.

This third group, containing red light-absorbing compounds, is comprised of compounds of the formula

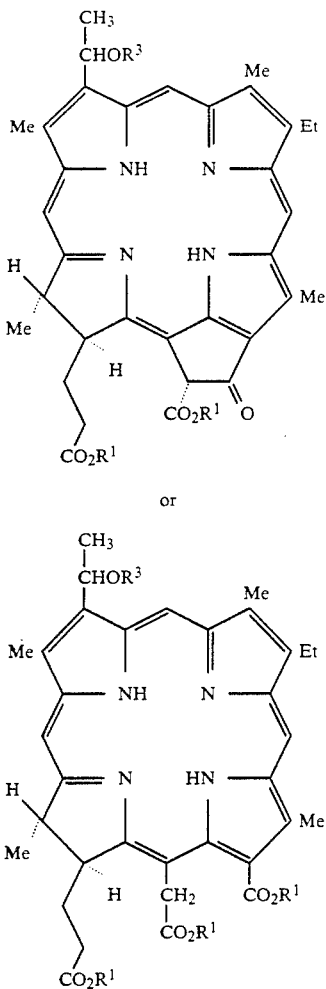

wherein $R^1$ is H or alkyl (1-6C) and $R^3$ is a hydrophobic group which is a saturated or unsaturated straight or branched chain hydrocarbyl of 4-25C. These are derivatized forms of the starting pheophorbol (formula 4) or chlorin e6 (formula 5). The compounds can be prepared by derivatization of the chlorophyll-derived tetrapyrole nucleus or its hydrolysate, as described below.

The starting material for preparation of the red light-absorbing compounds is methyl pheophorbide-a, which is isolated from *Spirulina deshidratada* by the method of Smith and Goff (D. Goff, Ph.D. Thesis, Univ. of Calif., Davis, Calif. 95616, 1984). Briefly, 500 gm dried Spirulina was slurried in a large volume of acetone and then liquid nitrogen was added to form a frozen slush. The slush was transferred to a 3 necked, 5 liter round bottom flask and heated to reflux under nitrogen with stirring for 2 hours. The mixture was filtered through Whatman paper on a Buchner funnel with extensive acetone washing. The extraction and filtration process was repeated 2 more times; all green color could not be removed from the solid.

The green filtrate was evaporated and purified by flash chromatography on Grade V neutral Alumina, eluting first with n-hexane to remove a fast running yellow band and then with dichloromethane to obtain the major blue/gray peak containing pheophytin-a. Treatment of pheophytin-a with 500 ml sulfuric acid in methanol for 12 hours at room temperature in the dark under nitrogen, was followed by dilution with dichloromethane. The reaction mixture was rinsed with water and then 10% aqueous sodium bicarbonate and the organic layer was dried, evaporated, and the residue recrystallized from dichloromethane/methanol to obtain 1.8 gm methyl pheophorbide-a. Methyl pheophorbide-a appears to be inactive in the in vivo tumorcidal activity assay when injected at a dose of 5 mg/kg; however, it is derivatized to the active compounds of the formula (4) above (pheophorbide derivatives) wherein $R^3$ is a hydrophobic straight or branched chain saturated or unsaturated hydrocarbyl group containing 4-25 carbons and its hydrolyzed forms of formula (5) (the chlorin derivative), wherein $R^3$ is as thus defined.

Conversion of methyl pheophorbide-a to the compounds of the invention is conducted by preliminary addition to the vinyl pi bond followed by substitution with the desired compound of the formula $R^3$—OH. The hexyl and phytyl derivatives were prepared as described in the examples below; hydrolysis to the corresponding chlorin was conducted on the starting material, which was then derivatized as exemplified below.

When tested in the in vivo tumorcidal assay, the $R^3$ ether derivatives of pheophorbol or of chlorin were comparably active to Photofrin II compositions. The phytyl ether of methyl pheophorbide-a gave excellent tumor response when injected at 1 mg/kg, although higher dosage levels showed problems with toxicity. Optimum results were obtained if the animals were irradiated after 48 hours, irradiation after only 3 hours subsequent to administration of the drug was ineffective.

Table 2 shows the results obtained using the hexyl ether of methyl pheophorbide-a or the hexyl ether of chlorin. Tumorcidal activity was clearly shown for these compounds.

TABLE 2

| Material | Dose mg/kg | Tumor Response Day 1-2 | Day 7 |
|---|---|---|---|
| Photofrin II | 4.2 (treated after 24 h) | 10/10 | 5/10 |
|  | 5.0 (treated after 24 h) | 10/10 | 7/10 |
| Methyl Pheo-a | 5.0 (treated after 24 h) | 0/10 |  |
| Hexyl ether deriv. of Methyl Pheo-a | 10 (treated after 6 days) | 5/5 | 3/5 |
|  | 0.5 (treated after 24 h) | 7/7 | 7/7 |
|  | 0.3 (treated after 24 h) | 10/10 | 9/10 |
| Hexyl deriv. of Chlorin e6 | 1.0 | 5/5 | 4/4 |
|  | 0.3 | 5/5 | 0/5 (day 4) |

Conjugates and Labeled Substances

In addition to using compositions which consist essentially of the above-defined compounds or preparations as active ingredient, it is possible to use derivatized forms of the tetrapyroles contained in order to provide a specific targeting mechanism. Commonly used target-specific components include monoclonal antibodies and ligands which bind to a cellular receptor. The compositions can also be conveniently labeled.

The target-specific component can then be, for example, an immunoglobulin or portion thereof or a ligand specific for a particular receptor. The immunoglobulin component can be any of a variety of materials. It may be derived from polyclonal or monoclonal antibody preparations and may contain whole antibodies or immunologically reactive fragments of these antibodies such as F(ab')$_2$, FAB, or FAB' fragments. Use of such immunologically reactive fragments as substitutes for whole antibodies is well known in the art. See, for example, Spiegelberg, H. L., in "Immunoassays in the Clinical Laboratory" (1978) 3:1-23.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L., supra.

Particularly useful antibodies include the monoclonal antibody preparation CAMAL1 which can be prepared as described by Malcolm, A., et al, *Ex Hematol* (1984) 12:539-547; polyclonal or monoclonal preparations of anti-M1 antibody as described by Mew, D., et al, *J Immunol* (1983) 130:1473-1477 (supra) and B16G antibody which is prepared as described by Maier, T., et al, *J Immunol* (1983) 131:1843; Steele, J. K., et al, *Cell Immunol* (1984) 90:303.

The foregoing list is exemplary and certainly not limiting; once the target tissue is known, antibody specific for this tissue may be prepared by conventional means. Therefore the invention is applicable to effecting toxicity against any desired target.

The ligand specific for receptor, refers to a moiety which binds a receptor at cell surfaces, and thus contains contours and charge patterns which are complementary to those of the receptor. It is well understood that a wide variety of cell types have specific receptors designed to bind hormones, growth factors, or neurotransmitters. However, while these embodiments of ligands specific for receptor are known and understood, the phrase "ligand specific for receptor", as used herein, refers to any substance, natural or synthetic, which binds specifically to a receptor.

Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine. Any analog of these substances which succeeds in binding to the receptor is also included.

The conjugation of the target-cell-specific component to the compounds of the invention can be effected by any convenient means. For proteins, such as Ig and certain receptor ligands, a direct covalent bond between these moieties may be effected, for example, using a dehydrating agent such as a carbodiimide. A particularly preferred method of covalently binding the compounds of the invention to the immunoglobulin moiety is treatment with 1-ethyl-3-(3-dimethylamino propyl) carbodiimide (EDCI) in the presence of a reaction medium consisting essentially of dimethyl sulfoxide (DMSO).

Of course, other dehydrating agents such as dicyclohexylcarbodiimide or diethylcarbodiimide could also be used as well as conventional aqueous and partially aqueous media.

Nonprotein receptor ligands can be conjugated to the dimers and trimers according to their relevant functional groups by means known in the art.

The active moieties of the conjugate may also be conjugated through linker compounds which are bifunctional, and are capable of covalently binding each of the two active components. A large variety of these linkers is commercially available, and a typical list would include those found, for example, in the catalog of the Pierce Chemical Co. These linkers are either homo- or heterobifunctional moieties and include functionalities capable of forming disulfides, amides, hydrazones, and a wide variety of other linkages.

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate to the target-specific component include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

The compounds of the invention per se or the conjugates may be further derivatized to a compound or ion which labels the drug. A wide variety of labeling moieties can be used, including radioisotopes and fluorescent labels. Radioisotope labeling is preferred, as it can be readily detected in vivo.

The compounds which are alone or are conjugates with a specific binding substance can be labeled with radioisotopes by coordination of a suitable radioactive cation in the porphyrin system. Useful cations include technetium and indium. In the conjugates, the specific binding substances can also be linked to label.

Administration and Use

The compounds and their conjugates with target-specific substances of the invention are useful, in general, in the manner known in the art for hematoporphyrin derivative and for Photofrin II compositions. These compositions are useful in sensitizing neoplastic cells or other abnormal tissue to destruction by irradiation using visible light—upon photoactivation, the compositions have no direct effect, nor are they entered into any biological event; however the energy of photoactivation is believed to be transferred to endogenous oxygen to convert it to singlet oxygen. This singlet oxygen is thought to be responsible for the cytotoxic effect. In addition, the photoactivated forms of porphyrin fluorescence which fluoresce can aid in localizing the tumor. Thus, the dimer and trimer compounds of the invention are not consumed or altered in exerting their biological effects.

Typical indications, known in the art, include destruction of tumor tissue in solid tumors, dissolution of plaques in blood vessels (see, e.g., U.S. Pat. No.

4,512,762); treatment of topical conditions such as acne, athletes foot, warts, papilloma, and psoriasis and treatment of biological products (such as blood for transfusion) for infectious agents, since the presence of a membrane in such agents promotes the accumulation of the drug.

The compositions are formulated into pharmaceutical compositions for administration to the subject or applied to an in vitro target using techniques known in the art generally. A summary of such pharmaceutical compositions may be found, for example, in *Remington's Pharmaceutical Sciences,* Mack Publishing Co., Easton, Pa., latest edition. The compositions labeled or unlabeled, can be administered systemically, in particular by injection, or can be used topically.

Injection may be intravenous, subcutaneous, intramuscular, or, even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

If the treatment is to be localized, such as for the treatment of superficial tumors or skin disorders, the compositions may be topically administered using standard topical compositions involving lotions, suspensions, or pastes.

The quantity of compound to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissue, such as those which comprise conjugates with a highly specific monoclonal immunoglobulin preparation or specific receptor ligand, dosages in the range of 0.05-1 mg/kg are suggested. For compositions which are less specific to the target tissue, larger doses, up to 1-10 mg/kg may be needed. The foregoing ranges are merely suggestive, as the number of variables in regard to an individual treatment regime is large and considerable excursions from these recommended values are expected.

EXAMPLES

The following examples are intended to illustrate the invention but not to limit its scope.

EXAMPLE 1

Hexyl Methyl Pheophorbide-a

A. The starting material, 50 mg methyl pheophorbide-a, described above, was reacted with HBr/acetic acid, with stirring in a sealed flask, at room temperature for 2.5 hours. The solvents were evaporated under high vacuum and the bromo derivative obtained was redissolved in 10 ml dry dichloromethane. To this was added 2 ml of dry n-hexanol and the reaction was stirred for 30 minutes, diluted in 10 ml dichloromethane and washed with water. The organic layer, was separated, dried over anhydrous sodium sulfate, and evaporated. The residue was purified using thin layer chromatography on silica and the desired product crystallized with dichloromethane/hexane in 70% yield. The structure of hexyl methyl pheophorbide was confirmed by NMR mass spectroscopy.

B. The corresponding phytyl methyl pheophorbide was prepared as described above using 2.5 ml phytyl alcohol in place of hexyl alcohol and the structure confirmed by mass spectroscopy.

EXAMPLE 2

Preparation of Chlorin-e6

The procedure of Smith and Bushell (M. J. Bushell, Ph.D. Thesis, Univ. of Liverpool, U.K., 1978) was used. The starting material, 1 gm of methyl pheophorbide-a, was dissolved in dry tetrahydrofuran (THF). To this was added sodium methoxide prepared by dissolving 200 mg sodium in 40 ml methanol, and the reaction was allowed to stir at room temperature for 1 hr. The mixture was poured into water and extracted with dichloromethane. The organic layer was washed with water, dried over anhydrous sodium sulfate and evaporated. The residue was dissolved in chloroform and treated with dichloromethane and ether, and the solid obtained was chromatographed on Alumina (Grade III) and eluted with toluene/dichloromethane 1/1. The major band, chlorin-e6 tetramethyl ester was recrystallized from dichloromethane/methanol to obtain 700 mg or 67% yield of the compound of formula

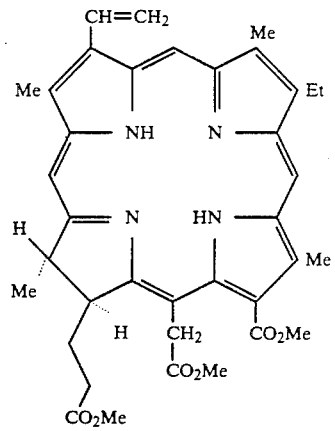

By re-utilizing the remaining starting material, an overall yield of 88.7% was obtained, and the structure was confirmed by NMR spectroscopy.

EXAMPLE 3

Preparation of the Hexyl Ether

The chlorin-e6 tetramethyl ester prepared in Example 2 (50 mg) was reacted with HBr/acetic acid and n-hexyl alcohol as described in Example 1 for methyl pheophorbide. The desired product was isolated in 68% yield, and the purity confirmed by TLC and HPLC. The structure was confirmed by NMR and mass spectroscopy; the spectra also showed evidence for aggregation of two chlorin units.

EXAMPLE 4

Hydrolysis of the Tetramethyl Ester 10 mg of the hexyl chlorin-e6 tetramethyl ester was dissolved in 5 ml distilled THF and 2 ml 1N NaOH was added. The reaction was stirred for 48 hours at room temperature under nitrogen and monitored by HPLC. Five ml distilled water was added and the mixture was extracted with dichloromethane to remove all THF. The aqueous layer was separated, freed of organic solvents by bubbling with nitrogen, and the pH was adjusted to 3.5 to precipitate the desired hexyl ether of chlorin-e6.

We claim:

1. A compound of the formula

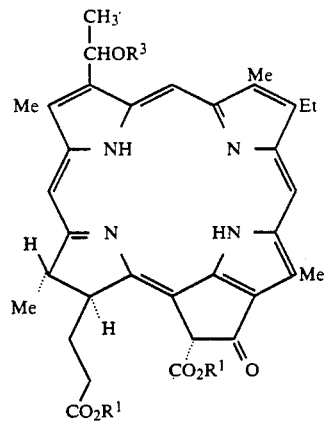

(4)

wherein $R^1$ is H or alkyl and $R^3$ is a hydrophobic group which is saturated or unsaturated, straight or branched chain hydrocarbon or 6-25C.

2. The compound as claimed in claim 1, wherein $R^3$ is hexyl.

3. A method to effect the destruction of target virus, cells or tissue, which comprises
contacting said target with an effective amount of compound of claim 1, followed by irradiation with light absorbed by said compound.

4. A method to effect the destruction of target virus, cells or tissue, which comprises contacting said target with an effective amount of the compound of claim 2, followed by irradiation with light absorbed by said compound.

5. A pharmaceutical composition useful in treatment of a target virus, cells or tissue, which comprises
an effective amount of the compound of claim 1
in admixture with a pharmaceutically acceptable excipient.

6. A pharmaceutical composition useful in treatment of a target virus, cells or tissue, which comprises:
an effective amount of the compound of claim 2; and
a pharmaceutically acceptable excipient material mixed with the compound of claim 2.

* * * * *